United States Patent [19]

Bushway

[11] Patent Number: 4,543,065
[45] Date of Patent: Sep. 24, 1985

[54] PRE-MADE REINFORCEMENT DEVICE

[76] Inventor: Geoffrey C. Bushway, Box 631, Tazewell, Va. 24651

[21] Appl. No.: 556,911

[22] Filed: Dec. 1, 1983

[51] Int. Cl.$^4$ .............................................. A61C 5/08
[52] U.S. Cl. .................................................. 433/221
[58] Field of Search ...................... 433/224, 220, 221

[56] References Cited

U.S. PATENT DOCUMENTS

| | | | |
|---|---|---|---|
| 453,703 | 6/1891 | Payne | 433/221 |
| 622,670 | 4/1899 | Dwight | 433/221 |
| 626,738 | 6/1899 | Underwood | 433/221 |
| 3,962,787 | 6/1976 | Corbett | 433/221 |
| 4,203,217 | 5/1980 | Kurer | 433/220 |
| 4,239,489 | 12/1980 | Ellman et al. | 433/220 |
| 4,348,183 | 9/1982 | Weissman | 433/221 |

FOREIGN PATENT DOCUMENTS 844341 7/1952 Fed. Rep. of Germany ...... 433/220

OTHER PUBLICATIONS

"Dental Products Report" Oct., 1983, (pp. 10, 16 & 92).

Primary Examiner—Robert Peshock
Attorney, Agent, or Firm—Fleit, Jacobson, Cohn & Price

[57] ABSTRACT

The present invention consists of a pre-made reinforcement device having a core for receiving a prosthetic crown. A vertical axis, horizontal plane anti-rotational device interconnects the post-and-core and is positioned within indexing recesses extending from a hole in the pretreated tooth. An advantageous locking of the reinforcement device results from the post, core and anti-rotational device combination.

21 Claims, 12 Drawing Figures

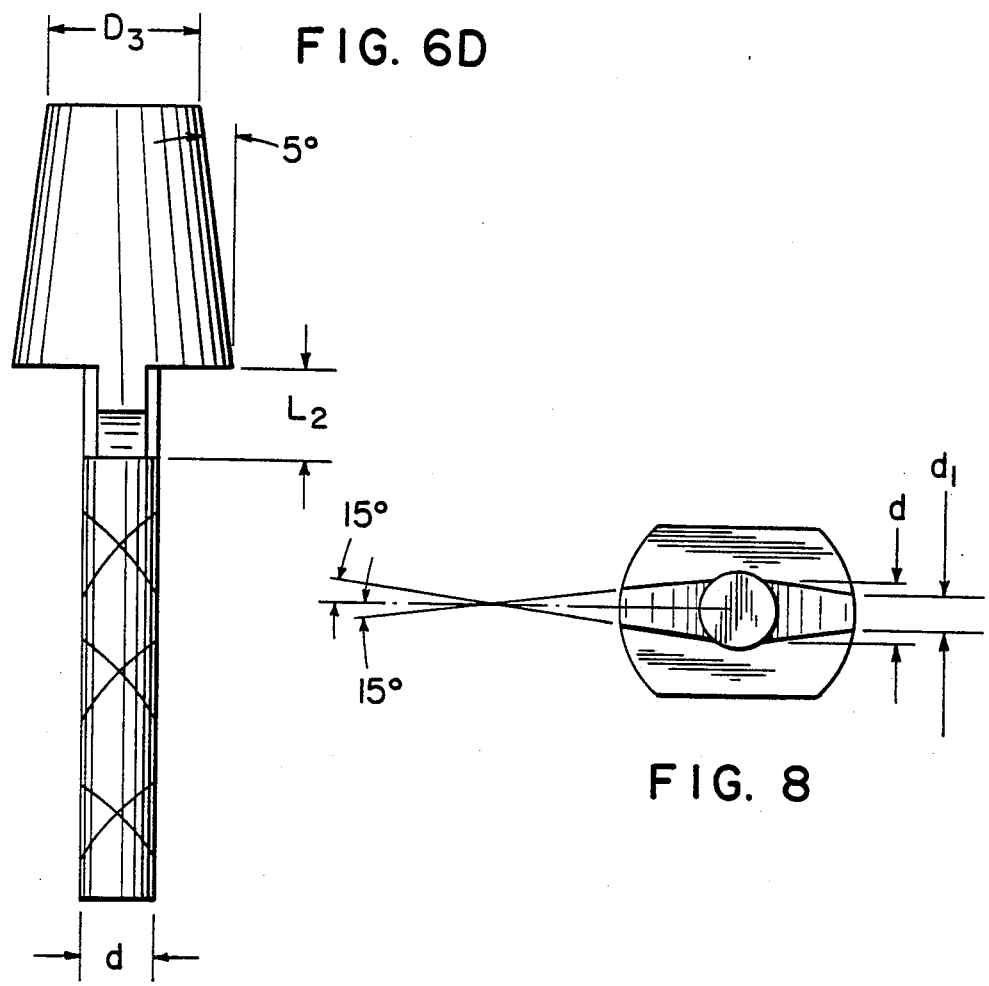
FIG. 6D
FIG. 8
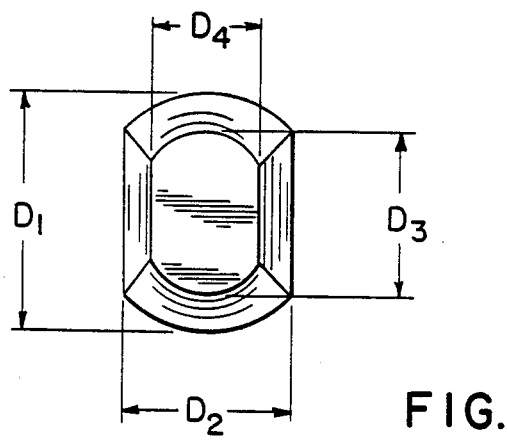
FIG. 7

PRE-MADE REINFORCEMENT DEVICE

BACKGROUND OF THE INVENTION

This invention relates to a system of pre-made reinforcement devices, commonly known as post-and-core systems, which fit into root-canal-treated teeth. This invention is applicable to all root canal treated teeth where the filling or obturation of the root canal by a dentist is done with modern methods and materials which use a thermoplastic or injection technique.

The purpose of the post in any post-and-core system in a root-canal-treated tooth is to reinforce the root structure about all three axes of rotation (horizontal, vertical and sagittal) when the root-canal-treated tooth is subjected to stress from the forces of mastication (chewing forces). The purpose of the core in any post-and-core system restoring a root-canal-treated tooth is to provide a tapered retention vehicle above a prepared root such that a dental fixed prosthesis will be retained when a dental cement is used. When the post-and-core is cemented into the root of the root-canal-treated tooth, they act together with the dental crown as one complete unit. The post, core and crown complex will act like, look like, and withstand forces as any virgin or non-root-canal-treated tooth. Ever since the development of techniques for filling root-canal-treated teeth, dentists have been searching for a simple, easily utilizable, and most important, a dependable design of post-and-core system to provide the "male" portion wherein the root would be the "female" portion.

All post-and-core systems are held in the prepared root by a dental cement in conjunction with a long post. The ideal length of the post is calcualted after measuring of the dental radiograph the distnce in millimeters from the apex of the tooth to the level of the interproximal bone. When using a "parallel-post" technique, the post should extend at least 6 millimeters apically from the coronal extent of the parallel preparation.

The post-hole in the root of the root-canal-treated tooth is prepared and shaped by any of several commercially available dental drills designed specifically for this purpose. The post-hole is slightly larger in diameter than the post. This is necessary to allow room for the cement and to prevent the post from engaging the sides of the walls of the post-hole preparation. Because a root-canal-treated tooth is prone to fracture, any excessive stress, such as the frictional stress created if the post were slightly larger than the post-hole, could create possible stress lines in the lateral walls of the post-hole preparation. The post is usually vented to allow the escape of dental cement as the post is inserted into a cement-filled post-hole. This venting reduces the likelihood of potential fracture lines being created in the apical end of the root due to compression of the dental cement.

Until recently, all techniques available for preparation of a post-and-core either had limitations with regard to accepting a practical post-and-core fabrication at the expense of reduced physical properties or producing an ideal post-and-core with maximum physical properties but with a technique that is demanding on the time and effort required by the dentist and on the financial investment required by the patient. The practical fabrication described above would include the use of dental amalgam or composite resin to form a core with a pre-made stock cylindrical post.

The other alternative available to the dentist would be a cast post-and-core wherein the post-and-core is fabricated first in wax or plastic either on a dental model or directly in the patient's mouth. Using this approach, the plastic or wax pattern is then processed into a metal post-and-core by a lost-wax casting process.

The core buildups of dental amalgam and composite resin have certain inherent limitations. The dental amalgam and composite resin core buildups condensed against commercially available pre-made cylindrical posts have certain weaknesses with regard to their limited strength when subjected to the forces of mastication. These forces placed on a tooth are in three planes and exert pressure on teeth in an anterior-posterior direction, a side-to-side direction, and an up-and-down direction, or any combination of these directions.

These facts are important because a technique will be described later which will prevent any post in a post-and-core system from rotating in a clockwise or counterclockwise direction. A significant percentage of failures in post-and-core systems takes place at the junction of the post-and-core and the tooth. Many of these failures are due to an inability of the post-and-core to resist rotational forces, also known as shearing forces.

It is appropriate at this point to describe the limitations of modern dental cements which are used by dentists. Most dental cements work on an ability to enhance physical interlocking of two surfaces in close approximation. There is significant evidence in professional literature that no true chemical bond exists between dental cement (regardless of the chemical formulation) and stainless steel posts, dental crowns, root canal post-hole preparations, or the lateral walls of the crown preparation of a non-root-canal vital tooth.

Many attempts at correcting failures of pre-made post-and-core systems have been made, but none have completely resolved two basic reasons for many post-and-core system failures. One reason for many failures is that the post bends due to stress from the forces of mastication. This problem can be solved by using a thicker post, i.e., a post with a larger diameter to give more thickness and strength to the post. Another significant reason for failures is the dislodgement of the post-and-core under the influence of rotational forces which place the cement union of the post-core and the tooth under shearing stress. Attempts at solving this latter problem include the use of retention pins in the core and the use of screw-in posts where the post is larger in diameter than the post-hole.

The use of commercially available retention pins for retaining dental amalgam or composite resin cores provides additional retention for the dental amalgam or composite resin core but does little to resist shearing forces. An additional problem with the retention pins is that their use may set up potential stress or fracture lines in the root-canal-treated tooth. In addition to doing very little to prevent a failure of the interface of the post and the core, the placement of retention pins presents a clear and persistent danger of precipitating a clinical fracture of the tooth.

The use of screw-in posts has been proposed as a solution to counteract the dislodging effect of shearing forces. With this system, the post is larger than the post-hole. The post is wedged or screwed in the post-hole preparation, with or without dental cement. The placement of the screw-in post places the lateral walls of the post-hole preparation under tension. The use of the screw-in post is questionable because the root of the root-canal-treated tooth is readily prone to fracture. A split tooth is a common problem associated with the use of a screw-in post. Also, the screw-in post only counteracts the effect of rotational forces in one direction. Assuming the screw-in post is screwed in and not placed in the post-hole preparation with a mallet, the dentist uses a clockwise rotational motion to advance the post into the post-hole. There is nothing in the design of a screw-in post, once it is seated completely, to oppose a counterclockwise force which tends to dislodge this type of post.

The present invention addresses many of the problems inherent in other pre-made post-and-core systems and a workable and practical solution will be described.

Accordingly, it is an object of the present invention to provide a pre-made system for reinforcing a root-canal-treated tooth by means of an anti-rotational device.

A further object of the present invention is to provide a pre-made post-and-core system which will eliminate clinical problems associated with currently available premade post-and-core systems.

A still further object of the present invention is to include a horizontal plane anti-rotational device which places dental cements under compressive rather than shearing forces when subjected to horizontal plane clockwise-counterclockwise forces from mastication.

SUMMARY OF THE INVENTION

A pre-made dental crown reinforcement appliance composed of a core, a post, and a horizontal plane anti-rotational device engages a pre-treated root-canal-tooth, and acts as an anchor for a prosthetic crown. The post fits in a hole in the tooth. The core is coaxial with the post. The pre-made dental crown reinforcement appliance can take the form of a three-component system, a two-component system or a combined unitary construction. The unique design of this post-and-core invention places dental cements under the force they are best able to resist—compressive forces—when a clockwise-counterclockwise shearing force is encountered.

Also, the design of the post-and-core of the present invention takes advantage of the use of an indexing groove placed in the tooth after the post-hole preparation is completed. The use of an indexing groove is well known within the dental community. Even in those teeth (especially maxillary and mandibular cuspids) where the root shape when viewed from the occlusal is elliptical—hence the nerve canal is elliptical—post-hole preparation frequently eliminates much of the elliptical shape of the nerve canal. When an extension of the core part of a post-and-core complex engages this indexing groove, a force in the horizontal plane in a clockwise-counterclockwise direction will subject dental cements to a compressive force.

BRIEF DESCRIPTION OF THE DRAWINGS

FIG. 6D is a side view of a post, core and anti-rotational device.

FIG. 7 is an overhead view of a core.

FIG. 8 is a view, from underneath of a post, core and two horizontal plane anti-rotational devices.

DETAILED DESCRIPTION OF THE DRAWINGS

The capabilities of the present invention are achieved in one embodiment through the use of three separate and distinct components. These will be referred to here after as Components A, B and C. Component A is a pre-made cylindrical post with a unique modification. The post comes in varying diameters in order to accommodate most sizes of post-holes.

Figure 1:
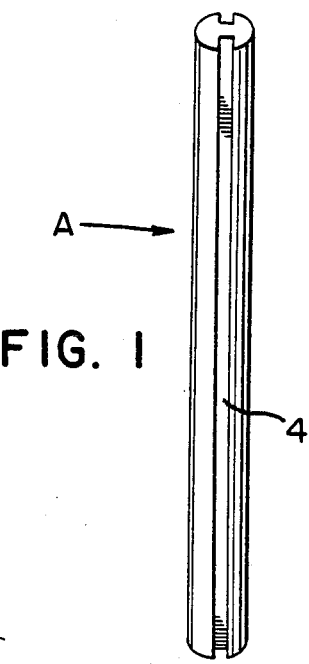
FIG. 1 is a side view of a post.

In FIG. 1 there are venting grooves 4 or indices cut along the long axis in Component A. The grooves are 180 degrees out of phase with each other and have a rectangular shape when viewed in cross section. The grooves have several purposes. One purpose is to vent the dental cement as the post is inserted into the post-hole. Venting grooves in the post prevent potential problems as the post is inserted in a cement-filled post-hole. These potential problems include extrusion of the dental cement into the periodontal ligament and periapical hard tissues (bone). The most common potential problem would be the incomplete seating of the post.

Figure 2:
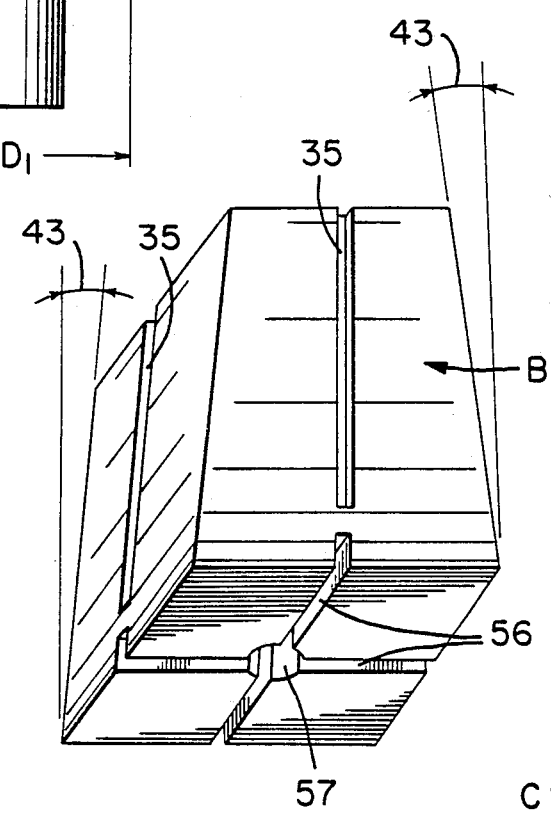
FIG. 2 is a perspective view of a core.

The Component B of the present invention is the core shown in FIG. 2. This Component B slides down over Component A. The hole in the center of Component B is slightly larger than the diameter of Component A. Component B as illustrated in FIG. 2 has opposing walls which are within about 5 to 7 degrees of parallism as shown by angle 43. In addition, each of the four walls of Component B has a retention groove 35. These four grooves act in conjunction with the taper and the truncated pyramid shape of Component B and will offer maximum retention and resistance to keep a dental crown from rotating under the influence of clockwise-counterclockwise forces. Slots are located in the base or larger end of Component B to hold a horizontal plane anti-rotational device, Component C.

The Component A and B complex of the post-and-core system is designed to eliminate many problems with regard to customizing and shaping a core in a post-and-core complex. The incorporation of an ideal taper and retention grooves in the design of Component B makes the dentist's job easier to create an ideal tooth preparation in areas where attaining this ideal preparation is difficult because of compromised intraoral access; i.e., in the maxillary molar region where the masseter or buccinator muscles and the coronoid process place a severe limitation on the ability of the dentist to get a handpiece into this area. Similar problems are encountered in the lower molar region.

Figure 3:
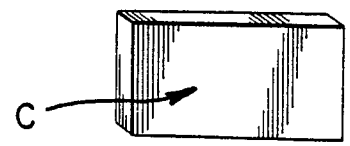
FIG. 3 is a perspective view of a horizontal plane anti-rotational device.
Figure 5:
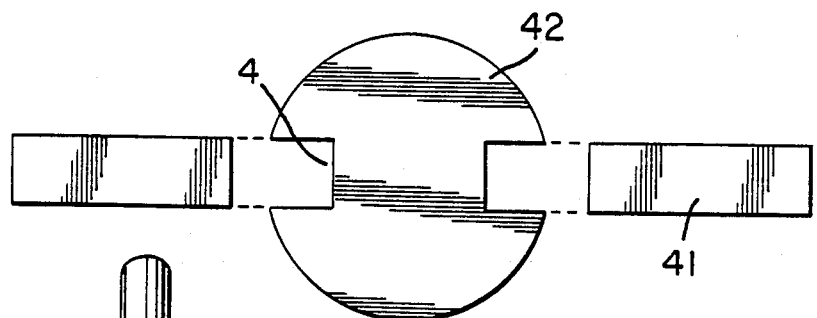
FIG. 5 is an overhead view of a post and horizontal plane anti-rotational devices.

The third component in the post-and-core system is Component C. In FIG. 3, Component C is a rectangular metal member acting as a horizontal plane anti-rotational device. This member fits into a slot at the larger end or base of the Component B. The design of the slots 56 at the base or larger end of Component B is such that the placement of Component C in these slots solves the problem of rotational forces adversely affecting a postand-core system. The slots in Component B are rectangular and Component C fits into these slots. The dimensions of Component C allow Component C to fit within an indexing groove cut into sound tooth structure at the coronal extent of the post-hole preparation. The indexing groove(s) in the tooth can be prepared with a straight fissure burr in a dental handpiece. Component C, after placement in the groove in Component B, is fin-like in that it extends apically beyond the base of Component B. Also, Component C extends beyond the limit of the interior wall of Component B to engage the venting or indexing slot 4 in Component A. This interior extension of Component C into Component A is only to the extent that it engages the indexing or venting slot in Component A. It does not impede the up-and-down motion of Component A through Component B. The lateral extent of the placement of Component C into the slot in Component B is such that Component C projects into the indexing groove cut in the tooth. This lateral extension of Component C does not prevent the complete seating of Component B into the tooth. Two indexing grooves can be cut into the tooth if adequate tooth structure remains.

Figure 4:
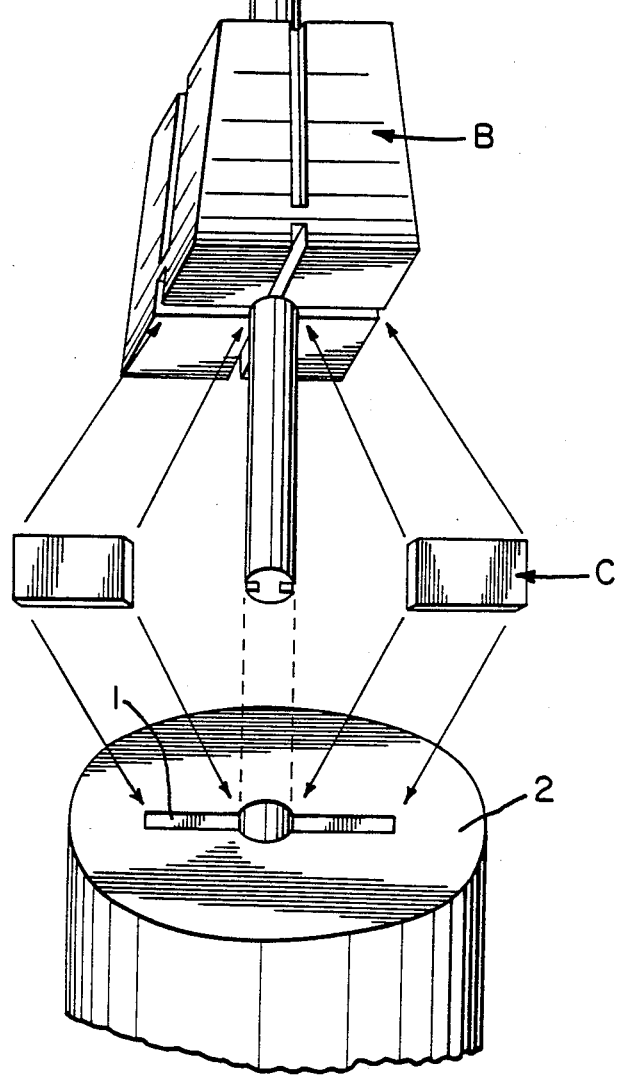
FIG. 4 is an exploded view of a post-and-core, two anti-rotational devices and a tooth prepared to receive a post, core and horizontal plane anti-rotational devices.

Components A and B are locked together by Component C in FIG. 4 by Component C's extension into the grooves of the Components A and B. Components A and B are locked into a tooth because Component C also extends into the indexing groove 1 in the tooth. Any clockwise or counterclockwise force in the horizontal plane influencing the Component A, B and C complex will be resisted by Component C's simultaneous engagement of Components A, B and the tooth 2. The horizontal plane anti-rotational device simultaneously interlocks the core, tooth and post structure and extends apically, coronally and medially from the core-tooth interface while simultaneously engaging the post.

The venting-indexing groove of the post increases the surface area in which the cement may be placed. With increased cement surface area, increased resistance to stress is achieved. Other forms of increasing the surface area of the post may be implemented by serrating, knurling, or scribing a screw or helix pattern on the post of approximately 80 grooves per inch, 0.003 inch deep by 0.230 inch minimum length.

After the Component A, B and C complex is cemented, any rotational force in the horizontal plane will place the dental cement in the stress situation its physical properties resist best, i.e., a crushing force because of the square shape of the indexing groove in the tooth and its counterpart, Component C.

A second embodiment of the present invention is detailed in FIGS. 6 through 8 and unites in a unitary construction some of the features characteristic of a multi-structure post-and-core complex. The single structure post-and-core in the present invention is coaxial in that the core is aligned directly over the post. This places all forces directly along the long axis of the tooth which is the most favorable physiologic relationship. The taper on the core is about 5 degrees per side. This ideal taper and length of the core provides for the prosthetic crown maximum resistance to occlusal displacement once the prosthetic crown is cemented. The modified-elliptical-cone shape (FIG. 7) of the core when viewed from the occlusal provides for the prosthetic crown maximum resistance to displacement under the influence of horizontal plane clockwise-counterclockwise forces.

In the herein described invention, the inclusion in the unitary post-and-core design of the horizontal plane anti-rotational device directly below the core provides for the post-and-core complex, a resistance to clockwise-counterclockwise forces once the post-and-core complex is cemented into the post-hole preparation. Also, the horizontal plane anti-rotational device is aligned with the long axis of the modified-elliptical-cone shape of the core when viewed from the occlusal. As most lower incisors, upper lateral incisors and all cuspids and bicuspids are elliptical-like when viewed in cross section from the occlusal at the cemento-enamel junction, the maximum amount of tooth will be present along this long axis of the elliptical-like coronal extent of the post-hole preparation of the root-canal-treated tooth. The indexing grooves can be placed in the tooth along this long axis. If adequate tooth structure remains for only one indexing groove, the extra anti-rotational device can be removed easily and quickly. The design and shape of the horizontal plane anti-rotational device is such that it fits into an indexing groove prepared within the tooth with a crosscut fissure burr. Frequently, adjustment is needed as it is not always possible to extend the indexing groove in the tooth the full length of the antirotational device. In those instances, the extra length and depth of the horizontal plane anti-rotational device can be reduced easily and quickly.

Typically, for maxillary and mandibular permanent incisors, the vertical plane is defined as being substantially parallel to the short axis of the modified elliptical-like core, the horizontal plane is perpendicular to the long plane of the post, and the sagittal axis is parallel to the long axis of the elliptical-like core.

Figure 9:
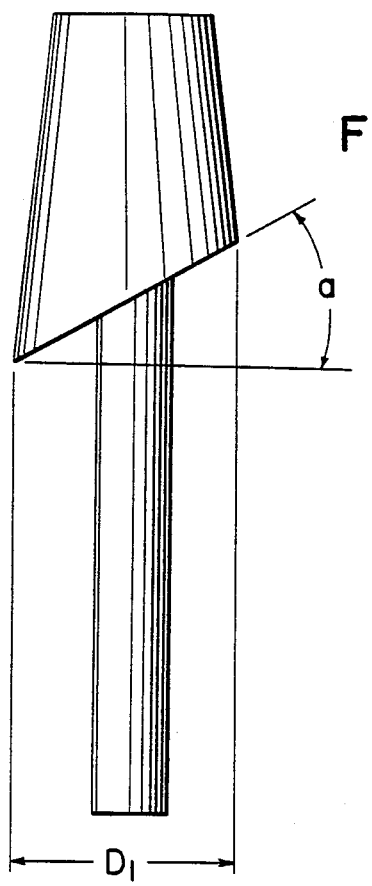
FIG. 9 is a side view of a post, core and horizontal plane anti-rotational device complex with an angled anti-rotational device.

For clinical situations where certain dimensions are increased, as in extreme gingival recession, the appropriate components of the post-and-core can be modified and adapted to meet the needs of most hard and soft dental anatomy as shown in FIG. 9. The angle "a" of the horizontal anti-rotational device is changed to complement gingival recession.

The complexes in the herein-described post-and-core system are typically fabricated from a stainless steel alloy. This stainless steel alloy has a very high resistance to deformation and corrosion. A series 300 stainless steel alloy may be used with a tensile strength of approximately 35,000 p.s.i. or greater.

Figure 6B:
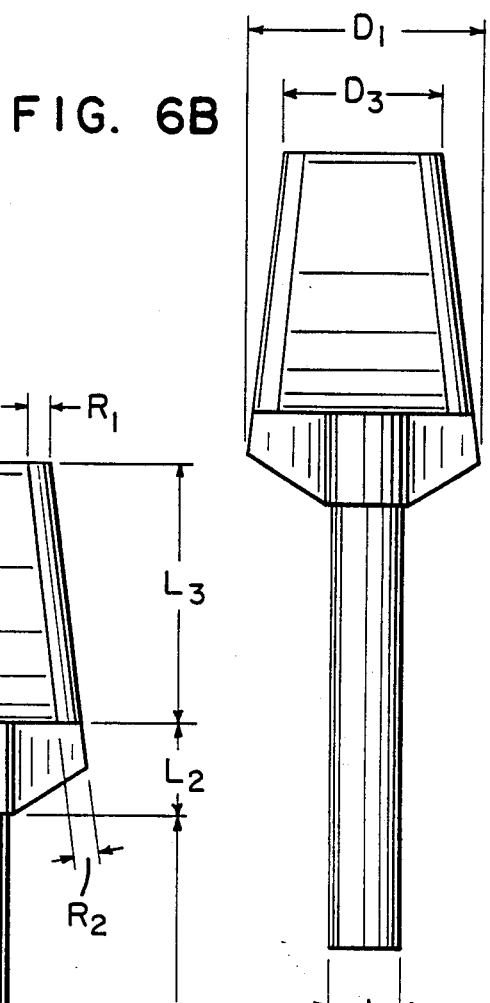
FIGS. 6A, 6B and 6C are a front views of a post, core and two anti-rotational devices.
Figure 6C:
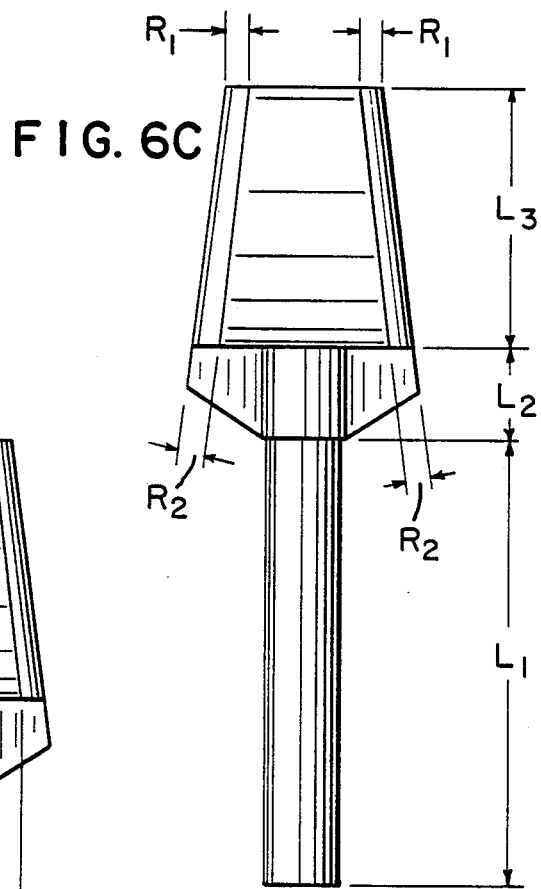

In FIG. 6C, $L_1$ is the length of the post, $L_2$ is the length of the horizontal plane anti-rotational device and $L_3$ is the length of the core. FIG. 6D shows the angle of convergence of the core to the vertical axis at 5° per side, with the angle of the core top to the vertical axis being 90°. In FIG. 6C, $R_2$ is the horizontal measurement in the side view of the unmilled portions along the core base. $R_1$ is the same measurement on the core top. $R_2$ is always greater than $R_1$.

In FIG. 7, $D_1$ is the long diameter of the core base, $D_2$ is the short diameter of the core base, $D_3$ is the long diameter of the core top and $D_4$ is the short diameter of the core top.

Figure 6A:
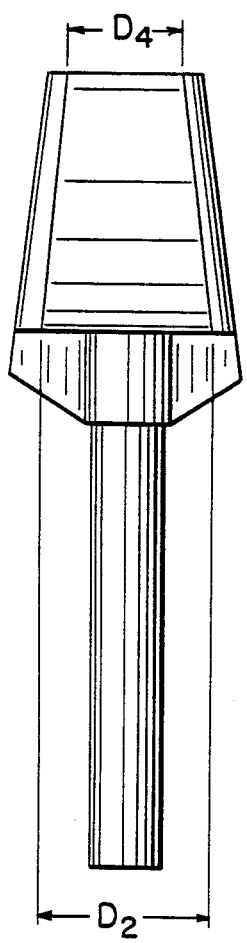

The flattened (milled) sides of the core illustrated in FIGS. 6A through 6C are substantially parallel to the horizontal plane anti-rotational devices. The magnitude of the depth of the flattening of the opposite sides is such that there is less flattening at the top of the core than at the base of the core. The intent of the flattening is to give an anti-rotational design to the prosthetic crown which will be cemented in place over the core.

In FIG. 8, the tapered portion of the horizontal plane anti-rotational device is displayed underneath the periphery of the core base. In a preferred embodiment, "$d_1$", is usually 0.030 inch regardless of "d" which is the diameter of the post. In an alternate embodiment, "$d_1$" may be equal to "d" to provide a rectangularly shaped anti-rotational device, when "d" is equal to or less than 0.038 inch. As "d" increases to approxiamtely 0.058 inch, "$d_1$" will remain 0.038 inch. As an aid to machining of the present invention, a cube with a height equal to $L_2$ and a depth and a width equal to "d" is machined at the area between the two anti-rotational devices, thus replacing a cylindrical portion of the post with a cubed portion.

In FIG. 9, "a" is the angle made by the long axis of the post and the horizontal plane anti-rotational device. This accommodation to gingival recession is usually not necessary, as indicated by the 90° angle "a" for the majority of post-and-core complexes shown in Table 1.

Table 1 illustrates some typical variations for the herein descried post-and-core system. Some typical dimensions for L1, L2 and L3 are 0.280, 0.075 and 0.240 inch, respectively.

TABLE 1

| $D_1/D_2$ | "d" | "a" | $D_1/D_2$ | "d" | "a" |
|---|---|---|---|---|---|
| 070/050 | 030 | 90 | 160/090 | 034 | 90 |
| 070/050 | 034 | 90 | 160/090 | 038 | 90 |
| 070/050 | 030 | 30 | 160/090 | 043 | 90 |
| 090/060 | 034 | 90 | 160/090 | 038 | 30 |
| 090/060 | 038 | 90 | 160/110 | 038 | 90 |
| 090/060 | 034 | 30 | 160/110 | 043 | 90 |
| 110/050 | 030 | 90 | 160/110 | 048 | 90 |
| 110/050 | 034 | 90 | 160/110 | 038 | 30 |
| 110/050 | 030 | 30 | 160/130 | 034 | 90 |
| 110/070 | 034 | 90 | 160/130 | 038 | 90 |
| 110/070 | 038 | 90 | 160/130 | 043 | 90 |
| 110/070 | 034 | 30 | 160/130 | 038 | 30 |
| 120/070 | 030 | 90 | 180/110 | 034 | 90 |
| 120/070 | 034 | 90 | 180/110 | 038 | 90 |
| 120/070 | 034 | 30 | 180/110 | 043 | 90 |
| 120/070 | 038 | 90 | 180/110 | 038 | 30 |
| 120/090 | 034 | 90 | 180/130 | 034 | 90 |
| 120/090 | 038 | 90 | 180/130 | 038 | 90 |
| 120/090 | 034 | 30 | 180/130 | 043 | 90 |
| 140/070 | 030 | 90 | 180/130 | 038 | 30 |
| 140/070 | 034 | 90 | 180/150 | 034 | 90 |
| 140/070 | 038 | 90 | 180/150 | 038 | 90 |
| 140/070 | 034 | 30 | 180/150 | 043 | 90 |
| 140/090 | 034 | 90 | 180/150 | 038 | 30 |
| 140/090 | 038 | 90 | 200/120 | 038 | 90 |
| 140/090 | 034 | 30 | 200/120 | 043 | 90 |
| 140/110 | 034 | 90 | 200/120 | 048 | 90 |
| 140/110 | 038 | 90 | 200/120 | 058 | 90 |
| 140/110 | 034 | 30 | 200/120 | 043 | 30 |
| 220/120 | 048 | 90 | 200/140 | 038 | 90 |
| 220/120 | 058 | 90 | 200/140 | 043 | 90 |
| 220/120 | 048 | 30 | 200/140 | 048 | 90 |
| 220/140 | 048 | 90 | 200/140 | 058 | 90 |
| 220/140 | 058 | 90 | 200/140 | 043 | 30 |
| 220/140 | 048 | 30 | 240/120 | 048 | 90 |
| 240/120 | 048 | 30 | 240/120 | 058 | 90 |
| | | | 240/120 | 048 | 30 |
| | | | 240/140 | 048 | 90 |
| | | | 240/140 | 058 | 90 |
| | | | 240/140 | 048 | 30 |

**$D_1$, $D_2$, and "d" are in thousandths of an inch, "a" is in degrees.

As will be readily understood by those of ordinary skill in the art, minor modifications may be made in the device described above without in any way departing from the spirit and scope of the invention. Specifcally, a two-piece embodiment may be used wherein any two components are joined such that they form a singular component. Moreover, it will be understood that the reinforcement device can be used in combination with prior art techniques for preparing a tooth for a root canal reinforcement device. Accordingly, it is understood that the invention will not be limited to the exact details disclsoed hereinabove, but will be defined in accordance with the appended claims.

I claim:

1. A reinforcement device for preventing rotation of a tooth crown, the tooth crown being connected to a root-canal-treated tooth having a post-hole with a central hole and two indexing grooves intersecting said central hole at an upper surface extending from said central hole, said device comprising:

an elongated post with at least one venting-indexing groove defined by said post, said post adapted to be seated within a post-hole of a root-canal-treated tooth;

a core acting as a retention vehicle for a tooth crown, said core defining a central hole and at least one indexing groove intersecting said central hole, said central hole of said core adapted to fit around said post and said core adapted to receive a prosthetic crown; and at least one horizontal plane anti-rotational device positioned contiguous with said post and said core and extending from said post substantially to the plane of an outer surface of said core, said anti-rotational device adapted to simultaneously engage an indexing groove of said tooth, said indexing groove of said core and said venting-indexing groove in said post.

2. A device according to claim 1, wherein said post, said core and said anti-rotational device are of a unitary construction.

3. A device as claimed in claim 1, wherein said post, said core and said anti-rotational device are formed as two pieces.

4. A device as claimed in claim 1, wherein said anti-rotational device decreases in thickness from a central region connected to said post to the plane of an outer surface of said core.

5. A device as claimed in claim 2, wherein said anti-rotational device decreases in thickness from a central region connected to said post to the plane of an outer surface of said core.

6. A device as claimed in claim 3, wherein said anti-rotational device decreases in thickness from a central region connected to said post to the plane of an outer surface of said core.

7. A device as claimed in claim 1, wherein said anti-rotational device is of a rectangular shape extending from a central region connected to said post to the plane of the outer surface of said core.

8. A device as claimed in claim 2, wherein said anti-rotational device is of a rectangular shape extending from a central region connected to said post to the plane of the outer surface of said core.

9. A device as claimed in claim 3, wherein said anti-rotational device is of a rectangular shape extending from a central region connected to said post to the plane of the outer surface of said core.

10. A device as claimed in claim 1, wherein said horizontal plane anti-rotational device is perpendicular to said post and adapted to engage said core indexing groove and said indexing groove of said tooth.

11. A device as claimed in claim 2, wherein said horizontal plane anti-rotational device is perpendicular to said post and adapted to engage said core indexing groove and said indexing groove of said tooth.

12. A device as claimed in claim 3, wherein said horizontal plane anti-rotational device is perpendicular to said post and adapted to engage said core indexing groove and said indexing groove of said tooth.

13. A device as claimed in claim 1, wherein there are two horizontal plane anti-rotational devices.

14. A device as claimed in claim 2, wherein there are two horizontal plane anti-rotational devices.

15. A device as claimed in claim 3, wherein there are two horizontal plane anti-rotational devices.

16. A device as claimed in claim 1, wherein said horizontal plane anti-rotational device extends apically, coronally and medially thus simultaneously engaging said tooth, said post and said core.

17. A device as claimed in claim 2, wherein said horizontal plane anti-rotational device extends apically, coronally and medially thus simultaneously engaging said tooth, said post and said core.

18. A device as claimed in claim 3, wherein said horizontal plane anti-rotational device extends apically, coronally and medially thus simultaneously engaging said tooth, said post and said core.

19. A device as claimed in claim 1, wherein said core is tapered to form a retention vehicle for a tooth crown.

20. A device as claimed in claim 2, wherein said core is tapered to form a retention vehicle for a tooth crown.

21. A device as claimed in claim 3, wherein said core is tapered to form a retention vehicle for a tooth crown.

* * * * *